(12) United States Patent
Sharma et al.

(10) Patent No.: US 12,340,894 B2
(45) Date of Patent: Jun. 24, 2025

(54) RECOMMENDING AT LEAST ONE IMAGING PROTOCOL FOR SCANNING A PATIENT

(71) Applicant: Siemens Healthcare GmbH, Erlangen (DE)

(72) Inventors: Sonal Sharma, Sawai Madhopur (IN); Karasani Krishna Teja, Guntur (IN)

(73) Assignee: Siemens Healthineers AG, Forchheim (DE)

( * ) Notice: Subject to any disclaimer, the term of this patent is extended or adjusted under 35 U.S.C. 154(b) by 457 days.

(21) Appl. No.: 17/868,338

(22) Filed: Jul. 19, 2022

(65) Prior Publication Data
US 2023/0048700 A1    Feb. 16, 2023

(30) Foreign Application Priority Data
Aug. 6, 2021   (DE) ..................... 10 2021 120 540.9

(51) Int. Cl.
*A61B 6/00*    (2024.01)
*G16H 30/20*    (2018.01)

(52) U.S. Cl.
CPC ............... *G16H 30/20* (2018.01); *A61B 6/54* (2013.01)

(58) Field of Classification Search
None
See application file for complete search history.

(56) References Cited

U.S. PATENT DOCUMENTS

| | | | |
|---|---|---|---|
| 9,317,580 B2 | 4/2016 | Cohen-solal et al. | |
| 2013/0311472 A1* | 11/2013 | Cohen-Solal | G16H 30/20 707/737 |
| 2014/0088984 A1 | 3/2014 | Oh et al. | |
| 2014/0365244 A1 | 12/2014 | Lee et al. | |
| 2015/0161329 A1 | 6/2015 | Mabotuwana et al. | |
| 2021/0193331 A1 | 6/2021 | Raman et al. | |

FOREIGN PATENT DOCUMENTS

| | | |
|---|---|---|
| EP | 2713177 B1 | 9/2015 |
| EP | 2798549 B1 | 2/2019 |

OTHER PUBLICATIONS

Schmidt, Teri M. Sippel, David Clunie, and Daniel Rubin. "IHE Radiology White Paper—Code Mapping in IHE Radiology Profiles." (Mar. 2014). pp. 1-37.

* cited by examiner

*Primary Examiner* — Dani Fox
(74) *Attorney, Agent, or Firm* — Lempia Summerfield Katz LLC

(57) ABSTRACT

The present disclosure relates to a system and a method for recommending at least one imaging protocol for scanning a patient. The method includes receiving, by a processor, an imaging protocol, wherein the imaging protocol includes information pertaining to set of imaging parameters for imaging a patient, determining at least one imaging identifier for the received imaging protocol based on a clinical intent of the received imaging protocol, determining at least one harmonized imaging protocol out of the plurality of harmonized imaging protocols based on the determined at least one imaging identifier, and providing the determined at least one harmonized imaging protocol on a graphical user interface.

19 Claims, 8 Drawing Sheets

RECOMMENDING AT LEAST ONE IMAGING PROTOCOL FOR SCANNING A PATIENT

The present patent document claims the benefit of German Patent Application No. 10 2021 120 540.9, filed Aug. 6, 2021, which is hereby incorporated by reference in its entirety.

TECHNICAL FIELD

The present disclosure relates to medical informatics and more particularly relates to a system and a method for recommending at least one imaging protocol for scanning a patient.

BACKGROUND

In the field of radiology, imaging procedures are performed every day to scan the patients for diagnosis. Each of such procedures require precise specifications such as a set of imaging parameters for accurately scanning the patient. In order to use precise specifications, such parameters are documented as a protocol. Such a documentation, especially in larger institutions is done manually by a group of expert radiologists, after peer-review, using standard, non-dedicated office applications such as a text processing program. The purpose of having written protocols is to provide consistency, for example, by making sure that patients with similar indications are examined the same way and to minimize errors in patient handling and protocol choice and adaptation. Protocols are also useful to train new radiologists and technologists.

Protocols may be developed for an individual institution having unique practices and local settings such as types of modalities, types of scanners, and types of procedures performed, e.g., a trauma center does not perform the same procedures as a cancer center. In particular, for larger institutions (e.g., network of hospitals covering a large population area), multiple radiology departments exist and over the years develop their own protocols, even if they interact frequently. As practice evolves over time, regular updates of these protocols are necessary to maintain efficiency, diagnostic accuracy, and quality of care. The protocols may be consistent throughout a given medical institution.

Such updates may be done through a committee of expert-radiologists or consultation with specialty doctors with an attempt to incorporate the latest knowledge or newer local practices and achieve a consensus within the radiology department(s). Unfortunately, editing and maintaining up-to-date protocols in a formalized way is a time-consuming activity, which requires high cooperation between the radiologists and technologists of an institution. As a consequence, in many radiology departments, there is no document or system describing the protocols. As such, the expertise and training of the radiologists and technologists is relied upon to assure a certain level of standardization.

Therefore, it is a challenge for radiologists and clinicians for interoperability of protocols across different machines. However, there is no such method or system available for standardizing or harmonizing the protocols and naming the protocols in such a way that it reflects the clinical intent of the imaging protocol. Furthermore, another challenge is that duplicate protocols may be created in the scanner for patients that require similar imaging protocol to be scanned. Moreover, another challenge is that the radiologists are required to tune the parameters from scratch every time a new patient is to be scanned. Such a process is time consuming and inefficient. Yet another challenge with the existing solution is that the solution does not provide a wholistic overview of protocols used across other imaging modalities, which limits the radiologist to rely only on previously stored imaging protocols or create new protocols based on one's expertise, thereby making the process time consuming.

In light of the above, there is a need for a method for recommending at least one imaging protocol for scanning a patient and naming the imaging protocols based on a set of rules thereby harmonizing the imaging protocols across different imaging modalities and institutions. Additionally, there is a need to harmonize the protocols with limited information about scan parameters and reconstruction parameters. Furthermore, the recommendation of the imaging protocols needs to be performed in a in a cost-effective, less time-consuming, and consistent way. Moreover, nomenclature and representation of imaging protocols representing meaningful information pertaining to clinical intent of the imaging protocol is required.

SUMMARY

The scope of the present disclosure is defined solely by the appended claims and is not affected to any degree by the statements within this summary. The present embodiments may obviate one or more of the drawbacks or limitations in the related art.

It is an object of the present disclosure to provide a system and a method for recommending at least one imaging protocol for scanning a patient. The method includes receiving, by a processor, an imaging protocol, wherein the imaging protocol includes information pertaining to set of imaging parameters for imaging a patient. Further, the method includes determining at least one imaging identifier for the received imaging protocol based on a clinical intent of the received imaging protocol. Herein, the determined imaging identifier is one out of a plurality of imaging identifiers which are stored in a first database. The first database includes a plurality of harmonized imaging protocols. Each of the harmonized imaging protocols is associated with at least one out of the plurality of imaging identifiers. Each of the plurality of imaging identifiers represents a clinical intent of the associated imaging protocol. Further, the method includes determining at least one harmonized imaging protocol out of the plurality of harmonized imaging protocols based on the determined at least one harmonized imaging identifier. Further, the method includes providing the determined at least one harmonized imaging protocol on a graphical user interface.

According to an embodiment, the method of providing the determined harmonized imaging protocol includes recommending the determined harmonized imaging protocol for scanning the patient, wherein the determined harmonized protocols are presented in a hierarchical manner.

According to an embodiment, the method further includes harmonizing the standard imaging protocols. The method includes obtaining, by the processor, a plurality of standard imaging protocols from one or more imaging modalities. Further, the method includes clustering each of the plurality of standard imaging protocols into a cluster, based on a clinical intent of the standard imaging protocols. Further, the method includes harmonizing each of the plurality of standard imaging protocols in each of the clusters with an imaging identifier and patient specific information. Further, the method includes storing the harmonized imaging protocols in the first database in a hierarchical manner based on a predefined set of rules.

According to an embodiment, the method of determining at least one imaging identifier includes mapping the received imaging protocol to an imaging identifier based on plurality of standard imaging protocols stored in a second database. Further, the method includes determining a mapping score of the mapping between the received imaging protocol and the mapped imaging identifier based on an accuracy of the mapping. Further, the method includes determining a cluster from a plurality of clusters stored in the first database when the mapping score is below a first threshold value, wherein each cluster in the plurality of clusters is associated with a harmonized imaging protocol based on a clinical intent of the information. Further, the method includes determining the imaging identifier associated with the determined cluster.

According to an embodiment, the method of determining the cluster from a plurality of clusters includes determining one or more features of the received imaging protocol, wherein the features include textual attributes of the imaging protocol and numerical attributes of the imaging protocol.

According to an embodiment, the method of determining a cluster from the plurality of clusters further includes calculating a distance variation between the received imaging protocol and each of the harmonized imaging protocols associated with the plurality of clusters based on the determined one or more features. Further, the method includes comparing each of the calculated distance variations with a second threshold value. Further, the method includes determining one or more harmonized imaging protocols having the distance variation above the second threshold value. Further, the method includes determining whether the one or more harmonized imaging protocols belong to the same cluster. Further, the method includes selecting the cluster when the one or more harmonized imaging protocols belong to the same cluster.

According to an embodiment, the method of determining a cluster from the plurality of clusters further includes calculating a difference between each of the numerical features of the imaging protocol and the numerical features of each of the one or more harmonized imaging protocols when the one or more harmonized imaging protocols do not belong to the same cluster. Further, the method includes determining at least one harmonized imaging protocol having the calculated difference below a third threshold value. Further, the method includes selecting the cluster associated with the determined at least one harmonized imaging protocol.

According to an embodiment, the method of determining a cluster from the plurality of clusters further includes calculating a slope variation between the obtained imaging protocol and each of the one or more harmonized imaging protocols when the calculated difference is above a fourth threshold value. Further, the method includes determining a harmonized imaging protocol having a calculated slope variation below the fourth threshold value. Further, the method includes selecting the cluster associated with the determined harmonized imaging protocol.

According to an embodiment, the method further includes generating a cluster for the received imaging protocol based on the set of imaging parameters when the calculated slope variation is above the fourth threshold value.

According to an embodiment, the method further includes determining an imaging identifier for the generated cluster based on a predefined set of rules.

According to an embodiment, the method further includes determining an imaging identifier for the obtained imaging protocol based on the second database when the mapping score is above the first threshold value.

According to an embodiment, the method further includes appending the imaging identifier associated with the imaging protocol with patient specific information, wherein the patient specific information includes an age of the patient, a weight of the patient, or a combination thereof.

The object of the disclosure is also achieved by an apparatus for recommending at least one imaging protocol for scanning a patient. The apparatus including at least one processor and a memory communicatively coupled to the at least one processor. The memory includes an imaging protocol recommendation module configured to perform the aforementioned method acts.

The object of the disclosure is also achieved by a system for recommending at least one imaging protocol for scanning a patient. The system includes a first database including a plurality of harmonized imaging protocols, a second database including a plurality of standard imaging protocols, and an apparatus as mentioned above.

The object of the present disclosure is also achieved by a computer-program product having machine-readable instructions stored therein, which when executed by one or more processors, cause the one or more processors to perform a method as described above.

The above-mentioned attributes, features, and advantages of this disclosure, and the manner of achieving them, will become more apparent and understandable (clear) with the following description of embodiments of the disclosure in conjunction with the corresponding drawings. The illustrated embodiments are intended to illustrate, but not limit the disclosure.

BRIEF DESCRIPTION OF THE DRAWINGS

The present disclosure is further described hereinafter with reference to illustrated embodiments shown in the accompanying drawings, in which.

DETAILED DESCRIPTION

Figure 1:
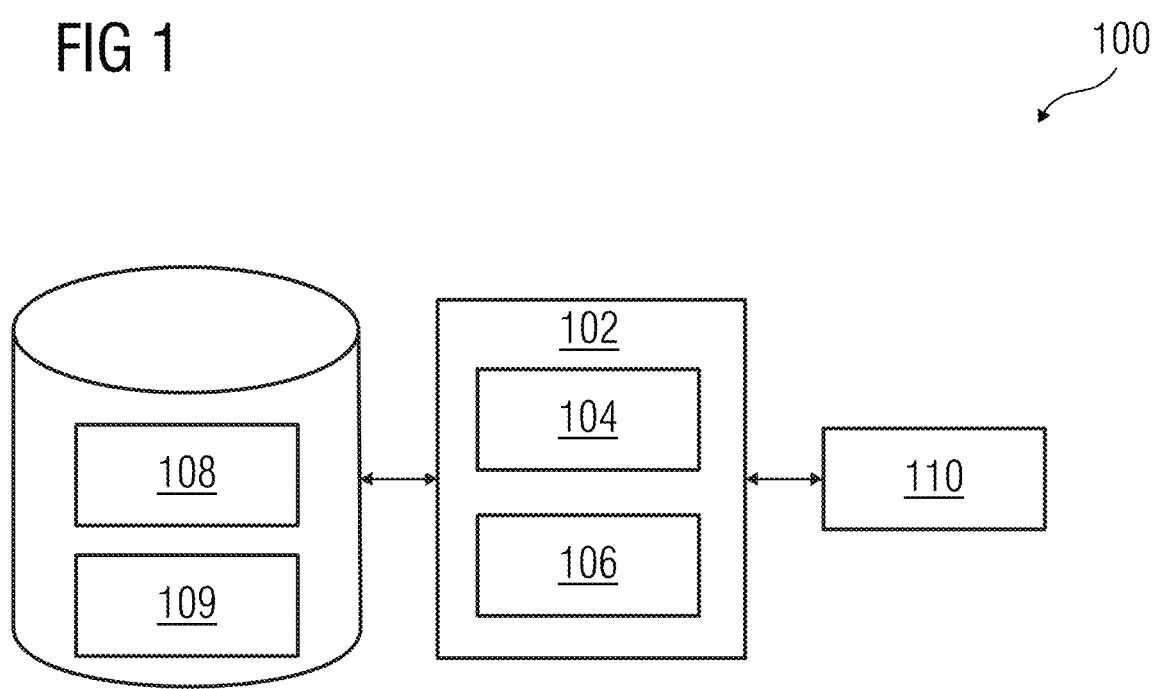
FIG. 1 illustrates a system for recommending at least one imaging protocol for scanning a patient, in accordance with an embodiment.

Hereinafter, embodiments for carrying out the present disclosure are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

Disclosed embodiments provide systems and methods for recommending at least one imaging protocol for scanning a patient. Throughout the present disclosure, the term "imaging protocols," as used herein, refers to a set of specifications required for performing imaging procedure a patient. Imaging protocols contain information that completely define the imaging procedures and serve as guidelines for imaging practices. Examples of such information include a unique name, a modality used (e.g., Computed Tomography (CT), Magnetic Resonance (MR), Nuclear Medicine (NM), X-rays (XR), Ultrasound (US), etc.), body area scanned (e.g., head, chest, etc.), list of clinical indications justifying the use of this specific protocol, list of types of imaging sequences and associated set of parameters, additional comments (e.g., describing the fact that this imaging procedure is a fast acquisition procedure to be used for uncooperative adults or non-sedated children), and patient handling (e.g., preparation, positioning in the scanner, administration of contrast agent, etc.).

Furthermore, the imaging protocols define the settings used on the imaging equipment to acquire the images and direct the imaging technologist who operates the scanner in how to perform the examination. The protocol as described here will result in an imaging study that includes one or more image series of different geometry or contrast, which in turn include one or more images. The selection of the protocol may occur before the patient is scanned.

For the purpose of the present disclosure, the term "imaging protocols" refers to the imaging protocols that have been customized by the user or clinician for scanning the patient. Hereinafter, imaging protocols received from the user are sometimes referred to as "customized imaging protocols."

Referring to FIG. 1, a system 100 for recommending at least one imaging protocol for scanning a patient is described, in accordance with an embodiment. The system 100 may be realized as a server-client arrangement or a cloud computing environment. In an exemplary implementation, the system 100 is a server-client arrangement 100. The system 100 includes an apparatus 102 that may be a remote server capable of providing cloud-based services such as data storage services, data simulation services, data visualization services, etc., based on the data from one or more user devices 110. The system 100 includes a processor 104, memory 106, a first database 108, a second database 109, and a user device 110. The apparatus 102, the first database 108, the second database 109, and the user device 110 are communicatively coupled to each other. The communication between the apparatus 102, the first database 108, the second database 109, and the user device 110 may be enabled via a communication network (not shown).

In some implementations, the apparatus 102 may be directly or indirectly coupled to communication network. For example, the apparatus 102 may be directly coupled to network via a hardwired network connection. Alternatively, the apparatus 102 may be wirelessly coupled to network via wireless communication channel established between the apparatus 102 and wireless access point (WAP) which in turn may be directly coupled to network. WAP may be, for example, an IEEE 802.11a, 802.11b, 802.11g, 802.11ac, 802.11ae, Wi-Fi®, RFID, and/or Bluetooth™ (including Bluetooth™ Low Energy) device capable of establishing wireless communication channel between user device and WAP. In other examples, the apparatus 102 may be wirelessly coupled to network via wireless communication channel established between the apparatus 102 and cellular network/bridge which may be directly coupled to network. User devices 110 may execute an operating system, examples of which may include but are not limited to, Android®, Apple® iOS®, Mac® OS X®, Red Hat® Linux®, or a custom operating system.

In some implementations, some or all of the IEEE 802.11x specifications may use Ethernet protocol and carrier sense multiple access with collision avoidance (e.g., CSMA/CA) for path sharing. The various 802.11x specifications may use phase-shift keying (PSK) modulation or complementary code keying (CCK) modulation, for example, Bluetooth™ (including Bluetooth™ Low Energy) is a telecommunications industry specification that allows devices such as mobile phones, computers, smart phones, and other electronic devices to be interconnected using a short-range wireless connection. Other forms of interconnection (e.g., Near Field Communication (NFC)) may also be used.

According to an embodiment, the apparatus 102 includes the processor 104 and the memory 106. Throughout the present disclosure, the term apparatus 102 as used herein refers to a structure and/or module that includes programmable and/or non-programmable components configured to store, process, and/or share information. Optionally, the apparatus 102 includes any arrangement of physical or virtual computational entities capable of enhancing information to perform various computational tasks. Furthermore, the apparatus 102 may be a single hardware server and/or a plurality of hardware servers operating in a parallel or distributed architecture. In an example, the apparatus 102 may include components such as memory, a processor, a network adapter, and the like, to store, process, and/or share information with other computing components such as user device/user equipment. Optionally, the apparatus 102 is a computer program that provides various services (such as database service) to other devices, modules, or apparatus.

In an embodiment, the system 100 includes the first database 108 (hereinafter, sometimes referred to as a harmonized imaging protocols database 108) including a plurality of harmonized imaging protocols associated with corresponding imaging identifiers. Additionally, the harmonized imaging protocols may also be associated with patient specific information. The term "database," with reference to the first database 108 and second database 109, may refer to a database (e.g., relational database, object-oriented database, triple store database, etc.) for storing harmonized imaging protocols and standard imaging protocols along with corresponding imaging identifiers and may be located within any suitable memory location, such as storage device coupled to the processor. In some implementations, patient information, imaging device specific information, etc., may be stored in the first database 108. The term "database," as used herein, refers to an organized body of digital information regardless of the manner in which the data or the organized body thereof is represented. Optionally, the database 108 is implemented using hardware, software, firmware, and/or any combination thereof. For example, the organized body of related data is in a form of a table, a map, a grid, a packet, a datagram, a file, a document, a list, or in any other form. The database includes any data storage software and systems such as a relational database like IBM DB2 and Oracle 9. Optionally, the database is used interchangeably herein as database management system, as is common in the art. Furthermore, the database management system refers to the software program for creating and managing one or more databases. Optionally, the database 108, when in operation, supports relational operations, regardless of whether it enforces strict adherence to the relational model, as understood by those of ordinary skill in the art. Additionally, the information is stored in the cells of the database 108.

The term "standard imaging protocols" refers to a set of standard specifications required for performing imaging procedure of a patient. In an example, the standard imaging protocols may be the imaging protocols that are considered as a healthcare standard defined by a group or association specializing in radiology. In another example, the standard imaging protocols may be the imaging protocols that are predefined by a manufacturer of an imaging modality (such as a CT scanner). Such standard imaging protocols are by defaults available in the scanner.

The term "harmonized imaging protocols" refers to a set of standard specifications required for performing imaging procedure of a patient that have been clustered and associated with imaging identifiers and patient specific information. In an example, the standard imaging protocols when harmonized to represent clinical intent of the protocol are referred to as harmonized imaging protocols. In another example, the harmonized imaging protocols may be the imaging protocols that have been historically used by the radiologists to perform particular imaging procedures. In another example, the harmonized imaging protocols may also be the customized imaging protocols that have been determined by the radiologists during an imaging procedure and harmonized to represent clinical intent.

The term "imaging identifiers" refers to an identifier associated with the imaging protocol that represents a clinical intent of the imaging protocol. The term "clinical intent," as used herein, refers to intent of the imaging protocol that is the basis for scanning the patient. Notably, the clinical intent is derived based on various fields available in the standard imaging protocols such as anatomies, purpose of study, scanning technique, and patient information.

The harmonized imaging protocols, imaging identifiers, and the association between the harmonized imaging protocols and corresponding imaging identifiers are stored in the first database 108. Furthermore, the first database 108 also includes a plurality of clusters. Herein, each cluster in the plurality of clusters is associated with a harmonized imaging protocol based on a clinical intent of the information. Notably, the clinical intent is derived based on various fields available in the harmonized imaging protocols such as anatomies, purpose of study, scanning technique, and patient information. Furthermore, the standard imaging protocols may be received from imaging modalities and other data repositories, and then harmonized to represent clinical intent of the imaging protocol. The harmonized protocols are then stored in the first database 108.

Once the imaging protocols are grouped into different clusters, the first database 108 is built. Furthermore, the first database 108 is continuously updated in case a new cluster is generated.

The processor 104 is configured to receive, by a processor, an imaging protocol, wherein the imaging protocol includes information pertaining to set of imaging parameters for imaging a patient. Further, the processor 104 is configured to determine at least one imaging identifier for the received imaging protocol based on a clinical intent of the received imaging protocol. The determined imaging identifier is one out of a plurality of imaging identifiers stored in a first database. The first database includes a plurality of harmonized imaging protocols. Each of the harmonized imaging protocols is associated with at least one out of the plurality of imaging identifiers. The plurality of imaging identifiers represents a clinical intent of the associated imaging protocol. Further, the processor 104 is configured to determine at least one harmonized imaging protocol out of the plurality of harmonized imaging protocols based on the determined at least one imaging identifier. Further, the processor 104 is configured to providing the determined at least one harmonized imaging protocol on a graphical user interface.

Figure 2:
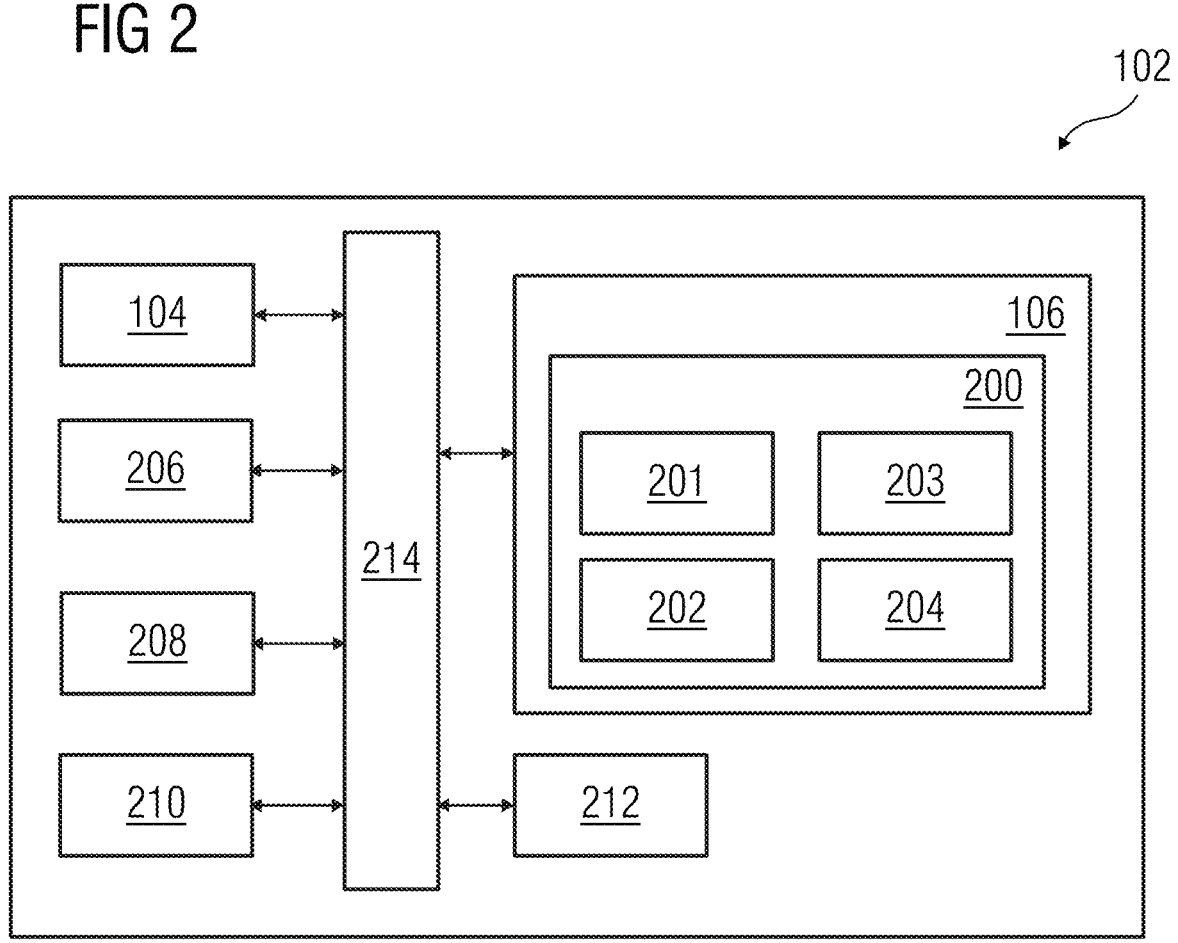
FIG. 2 illustrates an apparatus for recommending at least one imaging protocol for scanning a patient, in accordance with an embodiment.

Referring to FIG. 2, illustrated is an apparatus 102 for recommending at least one imaging protocol for scanning a patient, in accordance with an embodiment. The apparatus 102 includes a processor 104 for performing the method acts as aforementioned. The processor 104, as used herein, may refer to any type of computational circuit, including, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processor 104 may also include embedded controllers, such as generic or programmable logic devices or arrays, application specific integrated circuits, single-chip computers, and the like. A processor 104 may include hardware elements and software elements. The processor 104 may be configured for multithreading, e.g., the processor 104 may host different calculation processes at the same time, executing them either in parallel or switching between active and passive calculation processes.

The apparatus 102 includes a memory 106. The memory 106 may include a volatile memory and a non-volatile memory. The memory 106 may be coupled for communication with the processor 104. The processor 104 may execute instructions and/or code stored in the memory 106. A variety of computer-readable storage media may be stored in and accessed from the memory 106. The memory 106 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like.

Figure 3:
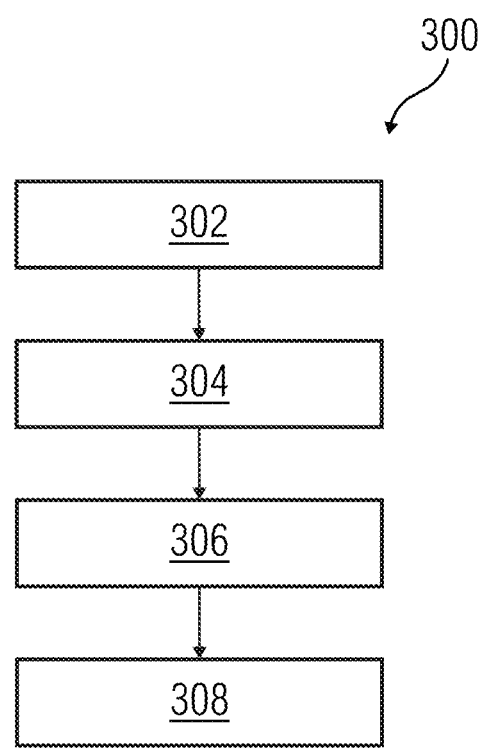
FIG. 3 illustrates a flowchart depicting acts of a method for recommending at least one imaging protocol for scanning a patient, in accordance with an embodiment.

The memory 106 includes an imaging protocol recommendation module 200 configured to perform the method acts as described in greater detail in FIG. 3. Furthermore, the imaging protocol recommendation module 200 includes a retrieval module 201, a protocol harmonization module 202, an imaging identifier determination module 203, and recommendation module 204. The imaging protocol recommendation module 200 is stored in the form of machine-readable instructions on any of the above-mentioned storage media and may be in communication to and executed by the one or more processors 104. The following description explains functions of the modules when executed by the one or more processors 104.

The retrieval module 201 is configured to obtain the standard imaging protocols from the plurality of imaging modalities. The retrieval module 201 may also obtain standard imaging protocols from data repositories. Further, the retrieval module 201 may also receive customized imaging protocols from a user device.

The protocol harmonization module 202 is configured to harmonize the standard imaging protocols and customized imaging protocols to represent the clinical intent of the imaging protocols. Further, the harmonization of imaging protocols includes associating a cluster to the imaging protocols and associating the imaging protocol with a name tag using predefined nomenclature.

The imaging identifier module 203 is configured for determining at least one imaging identifier for the received imaging protocol based on a clinical intent of the received imaging protocol. The determined imaging identifier is one out of a plurality of imaging identifiers stored in the first database 108. The first database 108 includes a plurality of harmonized imaging protocols. Each of the harmonized imaging protocols is associated with at least one out of the plurality of imaging identifiers. The plurality of imaging identifiers represents a clinical intent of the associated imaging protocol.

The recommendation module 204 is configured for providing the determined at least one harmonized imaging protocol on a graphical user interface associated with the user device 110. The determined harmonized imaging protocols are presented to the user or a clinician to view, compare, and use the recommended protocols for scanning the patient. Additionally, the determined harmonized protocols are presented in a hierarchical manner. "Hierarchical manner" is meant that the information about the harmonized imaging protocol is presented in a form of an ordered list from a higher clinical intent to a lower clinical intent. In an example, there will be complete hierarchy shown on the graphical user interface, which may include the scanner model, higher clinical intent, more precise clinical intent on the basis of keyword entered by the user or radiologist, patient specific clinical intent, and so forth. The presented recommendations may be variously highlighted (e.g., via color, size, outlining, etc.) and/or sorted (e.g., based on tissue of interest, etc.) in order of appropriateness to the patient. The recommendations may be displayed as user selectable options (e.g., graphical icons, menu options, etc.) and selected by the users via touchscreen technology, a mouse, a digital pen, a voice command (e.g., via voice recognition software), a keyboard, etc.

The apparatus 102 may further include a storage unit 206 that may be a non-transitory storage medium for storing metadata, threshold values, historical data, and so forth. Further, the apparatus includes a database 208, (e.g., which may include first database 108 and the second database 109 of FIG. 1), which stores the plurality of harmonized imaging protocols and plurality of standard imaging protocols with corresponding imaging identifiers, respectively. The apparatus 102 may further include an input unit 210 and an output unit 212. The input unit 210 may include input devices such as keypad, touch-sensitive display, camera (such as a camera receiving gesture-based inputs), etc. The input unit 210 is capable of receiving input signals such as inputs for receiving the imaging protocols, requests for recommending standard imaging protocols, and the like. The output unit 212 may be a user device (such as the user device 110 of FIG. 1) with a graphical user interface for recommendations of standard imaging protocols for scanning the patient based on the input from the user or radiologists, and so forth. The bus 214 acts as interconnection between the processor 104, the memory 106, the storage unit 206, the input unit 210, and the output unit 212.

Those of ordinary skill in the art will appreciate that the hardware depicted in FIGS. 1 and 2 may vary for different implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter, network connectivity devices also may be used in addition or in place of the hardware depicted. The depicted example is provided for the purpose of explanation only and is not meant to imply architectural limitations with respect to the present disclosure.

A system in accordance with an embodiment includes an operating system employing a Graphical User Interface. The operating system permits multiple display windows to be presented in the Graphical User Interface simultaneously with each display window providing an interface to a different application or to a different instance of the same application. A cursor in the Graphical User Interface may be manipulated by a user through the pointing device. The position of the cursor may be changed and/or an event such as clicking a mouse button, generated to actuate a desired response.

One of various commercial operating systems, such as a version of Microsoft Windows™ may be employed if suitably modified. The operating system is modified or created in accordance with the present disclosure as described.

The present disclosure is not limited to a particular computer system platform, processor, operating system, or network. One or more aspects of the present disclosure may be distributed among one or more computer systems, for example, servers configured to provide one or more services to one or more client computers, or to perform a complete task in a distributed system. For example, one or more aspects of the present disclosure may be performed on a client-server system that includes elements distributed among one or more server systems that perform multiple functions according to various embodiments. These elements include, for example, executable, intermediate, or interpreted code, which communicate over a network using a communication protocol. The present disclosure is not limited to be executable on any particular system or group of systems, and is not limited to any particular distributed architecture, network, or communication protocol.

Referring to FIG. 3, in conjunction with FIGS. 1 and 2, a flowchart depicting acts of a method 300 for recommending at least one imaging protocol for scanning a patient is described, in accordance with an embodiment. The method 300 includes acts 302 to 308 and may be implemented on the system 100.

At act 302, the imaging protocol including information pertaining to a set of imaging parameters for imaging a patient is received. The imaging protocol may be received from the user device 110. The imaging protocol may be determined based on clinical indications of the patient on whom the scanning is to be performed. The imaging protocol may be determined by the radiologist performing the scan. In an example, the imaging protocol is determined by the radiologist based on the clinical indications such as one or more symptoms of the patient. In an example, clinical indications for a patient may include symptoms such as "hearing loss in left ear," with the note to perform an "MRI of the head." Within this examination type, there are many options of clinical imaging protocols that are used specifically by the imaging center or radiology department. Examples that are under the category "MRI of the head" may include "brain tumor," "multiple sclerosis," "angiography," "MR without contrast," "internal auditory canal," "eye-orbit," and so forth. A radiologist reading this order may decide that the order is best fulfilled by using the "internal auditory canal" protocol. Subsequently, the radiologists determine a set of imaging parameters for operating an imaging modality. Non-limiting examples of imaging modality or medical device may be ultrasound imaging device, CT, magnetic resonance imaging (MRI), functional MRI (e.g., fMRI, DCE-MRI, and diffusion MRI), cone beam computed tomography (CBCT), Spiral CT, positron emission tomography (PET), single photon emission computed tomography (SPECT), X-ray, optical tomography, fluorescence imaging, ultrasound imaging, radiotherapy portal imaging, and so forth. Once the imaging protocol is determined by the radiologist, the information pertaining to the imaging protocol is entered in the user device as input data. In another example, one or more keywords based on clinical indications of the patient such as "MRI of the head," "knee MRI," "angiography," and so forth may also be entered as input data to the user device 110. Subsequently, the one or more keywords and/or imaging protocol is received by the processor 104 for further processing.

At act 304, at least one imaging identifier for the received imaging protocol based on the clinical intent of the received imaging protocol. Herein, the determined imaging identifier is one out of a plurality of imaging identifiers which are stored in the first database 108. The first database 108 includes a plurality of harmonized imaging protocols. Furthermore, each of the standard imaging protocols is associated with at least one out of the plurality of imaging identifiers. Herein, each of the plurality of imaging identifiers represents a clinical intent of the associated imaging protocol. The method of harmonizing the imaging protocols is explained in greater detail in FIG. 4. Furthermore, the method of determining at least one imaging identifier is explained in greater details in FIG. 5.

At act 306, at least one standard imaging protocol is determined out of the plurality of the harmonized imaging protocols based on the determined at least one imaging identifier. Notably, the association between the harmonized imaging protocols and corresponding imaging identifiers are stored in the first database 108, and hence the processor 104 is configured to determine the harmonized imaging protocol based on the determined imaging identifier.

At act 308, the determined at least one harmonized imaging protocol is provided on a graphical user interface. The graphical user interface is associated with the user device 110. According to an embodiment, providing the determined standard imaging protocol includes recommending the determined harmonized imaging protocol for scanning the patient in a hierarchical manner. In an example, the determined standard imaging protocols may be provided to the radiologist as list of imaging protocols. The radiologist may choose the most suitable imaging protocol for scanning the patient. "Hierarchical manner" means that the information about the harmonized imaging protocol is presented in the form of an ordered list from a higher clinical intent to a lower clinical intent. In an example, there will be complete hierarchy shown on the graphical user interface which may include the scanner model, higher clinical intent, more precise clinical intent on the basis of keyword entered by the user or radiologist, patient specific clinical intent, and so forth. The representation of the harmonized imaging protocols in a hierarchical manner provides the radiologist with a set of harmonized imaging protocols to choose from. In an example, the radiologist may choose from the provided list based on a number of parameters such as dose quantity, time required, quality of the scan, and so forth. Not only standard protocols are presented to the user, but all the available harmonized protocols including standard imaging protocols and customized imaging protocols related to the particular clinical intent available in a particular institution will be shown. The imaging identifier of the determined harmonized imaging protocol represents similar clinical intent to the received imaging protocol. This method eliminates creating multiple protocols for similar clinical intent, thereby standardizing the imaging protocols for scanning the patients.

Figure 4:
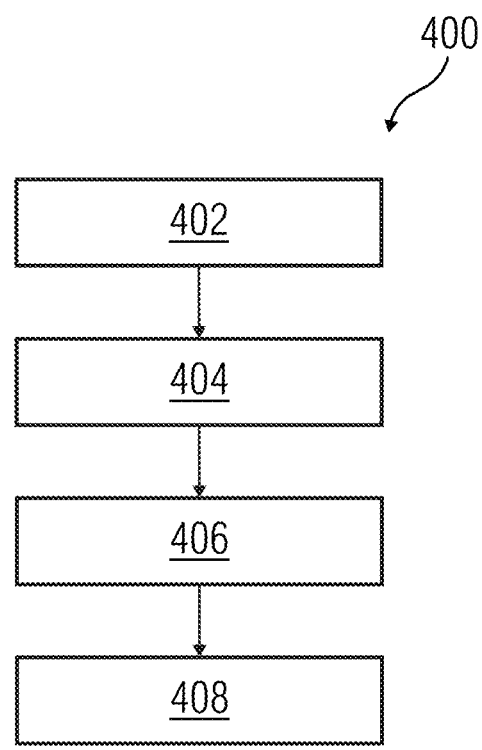
FIG. 4 illustrates a flowchart depicting acts of a method for harmonizing a plurality of standard imaging protocols, in accordance with an embodiment.

Referring to FIG. 4, a flowchart 400 depicting acts of a method for harmonizing the imaging protocols is illustrated, in accordance with an embodiment. At act 402, a plurality of standard imaging protocols is received from one or more sources. Herein, the one or more sources refer to devices or data storage units from where the standard imaging protocols may be obtained. In an example, the one or more sources may include one or more imaging modalities that may be a part of an institution such as a hospital. In another example, the one or more sources may be data repositories that store standard imaging protocols. Furthermore, the standard imaging protocols may be obtained from one or more sources such as data repositories. In the context of radiology use case scenario, the one or more data repositories may include one or more of a picture archiving and communication system (PACS), Radlex Playbook Identifiers (RPID) a radiology information system (RIS), a hospital information system (HIS), an electronic medical record (EMR), a database, a server, an imaging system, a computer, and/or other data repository. Such data may be stored in standard formats such as Digital Imaging and Communications in Medicine (DICOM) and/or other standard formats, and/or non-standard, proprietary, and/or other format. The standard imaging protocols and corresponding imaging identifiers are obtained and are classified into the plurality of clusters based on the clinical intent of the standard imaging protocols.

At act 404, each of the plurality of standard imaging protocols are grouped into a cluster based on a clinical intent of the standard imaging protocols. In an embodiment, a plurality of imaging protocols is collected and grouped into multiple clusters based on clinical intent obtained from set of imaging parameters or a subset of relevant imaging parameters. Therefore, imaging protocols for which the parameters are identical or for which the parameters have changed only slightly are grouped together. Various cluster algorithms may be employed, such as, but not limited to, k-means, c-means, self-organizing maps, or hierarchical clustering algorithms. Several approaches may be used, individually or in combination, to cluster the standard imaging protocols. For example, in one instance, an ontology-based approach is used to identify synonyms or to group medical concepts related through a parent-child relationship or other relationships. Optionally, a statistical approach that highlights significant associations between terms and groups them as related may be utilized. Significant associations between medical terms may be obtained from different sources to cluster the imaging protocols and build the database of these known associations. They may be built manually by medical experts or they may be derived from data. In the latter case, the associations may be identified through co-occurrence frequencies between medical concept terms in a collection of reports, scholarly articles (e.g., medical journals), or clinical textbooks on specific domains. To extract the most significant associations, statistical techniques may be applied like the Fisher's exact test or Chi-square tests.

At act 406, harmonizing each of the plurality of standard imaging protocols in each of the clusters with an imaging identifier and patient specific information. "Harmonization" means that the each of the standard imaging protocols are clustered into corresponding clusters based on similarity as stated above. Additionally, the imaging protocol is associated with an imaging identifier when assigned to the cluster. Furthermore, harmonization of the imaging protocols also includes appending the imaging protocol with specific information such as information about scanner; information about patient age, height, or weight; information about dosage of radiation; information about time required for the scan; and so forth.

At act 408, storing the harmonized imaging protocols in the first database in a hierarchical manner. The information of the harmonized imaging protocol is arranged in a hierarchical manner based on a predefined set of rules. A dictionary is created for the harmonized imaging protocols based on the predefined set of rules. The predefined set of rules are based on anatomy, sub-anatomy, process, study type levels for describing the hierarchy, and so forth. The multiple levels of information obtained from the imaging protocol name and categorical data is arranged using this set of rules for maintaining the hierarchy. Furthermore, additional study details and patient information of available for customized imaging protocols are appended with the hierarchy for creating the name tags or identifiers for the imaging protocols.

Figure 5:
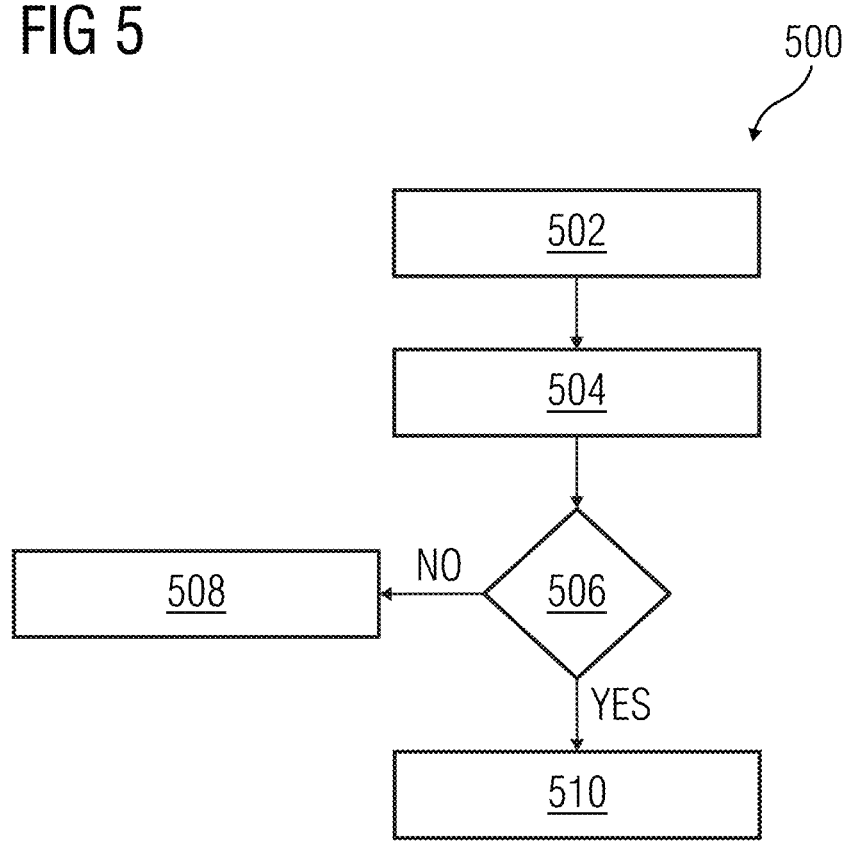
FIG. 5 illustrates a flowchart depicting acts of a method for determining at least one imaging identifier, in accordance with an embodiment.

Referring to FIG. 5, a flowchart 500 depicts acts of a method for determining at least one imaging identifier is illustrated in accordance with an embodiment. At act 502, the received imaging protocol to an imaging identifier based on plurality of standard imaging protocols stored in the second database 109. Herein, the second database 109 includes a Radlex Playbook including a plurality of harmonized imaging protocols and corresponding Radlex playbook identifiers for reference. The received imaging protocol is mapped to each of the standard imaging protocols stored in the second database 109. According to an embodiment, the imaging protocols received by the processor 104 are preprocessed before further processing such as mapping the received imaging protocol. Notably, the preprocessing of the information in received imaging protocol includes techniques such as data cleaning. In an example, the information from the text fields in the received imaging protocol are combined as a single string. Additionally, words which do not carry information about the clinical intent of the imaging protocol are removed from the single string. In an example, words related to anatomical region, body size, and protocol name such as the machine name or institute name are removed during data cleaning. Further, the data cleaning and domain specific preprocessing techniques are performed to replace generic words in the imaging protocol with Radlex specific words. For example, Angio/Angiogram is replaced with Angiography using the predefined set of rules. The preprocessing of the information of the imaging protocols helps in normalizing the data and provide accurate results of mapping.

At act 504, a mapping score of the mapping between the received imaging protocol and the mapped imaging identifier is determined based on an accuracy of the mapping. The mapping score is a quantitative measure of the accuracy of mapping between the received imaging protocol and the mapped imaging identifier. In an example, the combined string is compared against the second database 109 based on a similarity measuring technique, for example, Jaccard average similarity or Jaccard similarity index. The Jaccard similarity index compares members for two sets to see which members are shared and which are distinct. The Jaccard similarity index is a measure of similarity for the two sets of data, with a range from 0 to 1. The higher the percentage, the more similar the two datasets which are being mapped with each other. The Jaccard average similarity is given by:

$$J(A, B) = \frac{\#(A \cap B)}{Avg(\#(A), \#(B))}$$

Normalizing the similarity index using the average of the string lengths (of A and B) is better when A and B are dissimilar with long length, and wherein $\#(A \cap B)$ reduces the overall similarity index value. The calculated value of mapping score determines whether or not the received imaging protocol may be accurately associated with a corresponding standard imaging protocol having a similar clinical intent.

In case there is an exact matching based on the combined string, then the mapping score may be 1. Furthermore, when an exact match for the received imaging protocol is not found in the Radlex Playbook, then the mapping score may be 0.9, 0.8, 0.7, 0.6, 0.5, 0.4, 0.3 and so forth.

At act 506, the determined mapping score is compared with a first threshold value to determine whether the mapping score is below the first threshold value of above the first threshold value. The first threshold value may be a numerical value of accuracy of mapping below which the accuracy of mapping is not considered as optimal. In an example, the first threshold value may be a value 0.3. The first threshold value is a predetermined value based on a standard which may be considered as a mapping score which yields an accurate mapping between received imaging protocol and standard imaging protocols. Herein, act 508 is executed when the mapping score is above the first threshold value and act 510 is executed when the mapping score is below the first threshold value.

At act 508, an imaging protocol identifier is determined for the obtained imaging protocol based on the second database 109 when the mapping score is above the first threshold value. In an example, when the mapping score between the received imaging protocol is above the first threshold value, the RPID having the highest mapping score is selected from the Radlex Playbook. Subsequently, the standard imaging protocol corresponding to the selected RPID is recommended to the radiologist for scanning the patient.

At act 510, a cluster is determined from a plurality of clusters stored in the first database 108 when the mapping score is below the first threshold value. Herein, each cluster in the plurality of clusters is associated with a harmonized imaging protocol based on the clinical intent of the information. The term "cluster," as used herein, refers to a set of imaging protocols that are grouped together based on similar clinical intent of the imaging protocols. Each cluster in the plurality of clusters is associated with an imaging identifier. Therefore, each of the imaging protocols that belongs to the same cluster is associated with the same imaging identifier. In an example, an imaging protocol for scanning the foot of the patient and imaging protocol for scanning the ankle of the patient may have similar clinical intent and may be grouped together in one cluster. The method of determining the cluster from the plurality of clusters is explained in greater detail in FIGS. 6, 7, and 8.

In a subsequent act in the method disclosed within FIG. 5, an imaging identifier associated with the determined cluster may be determined. Subsequently, the standard imaging protocol corresponding to the determined imaging identifier is recommended to the radiologist for scanning the patient.

Figure 6:
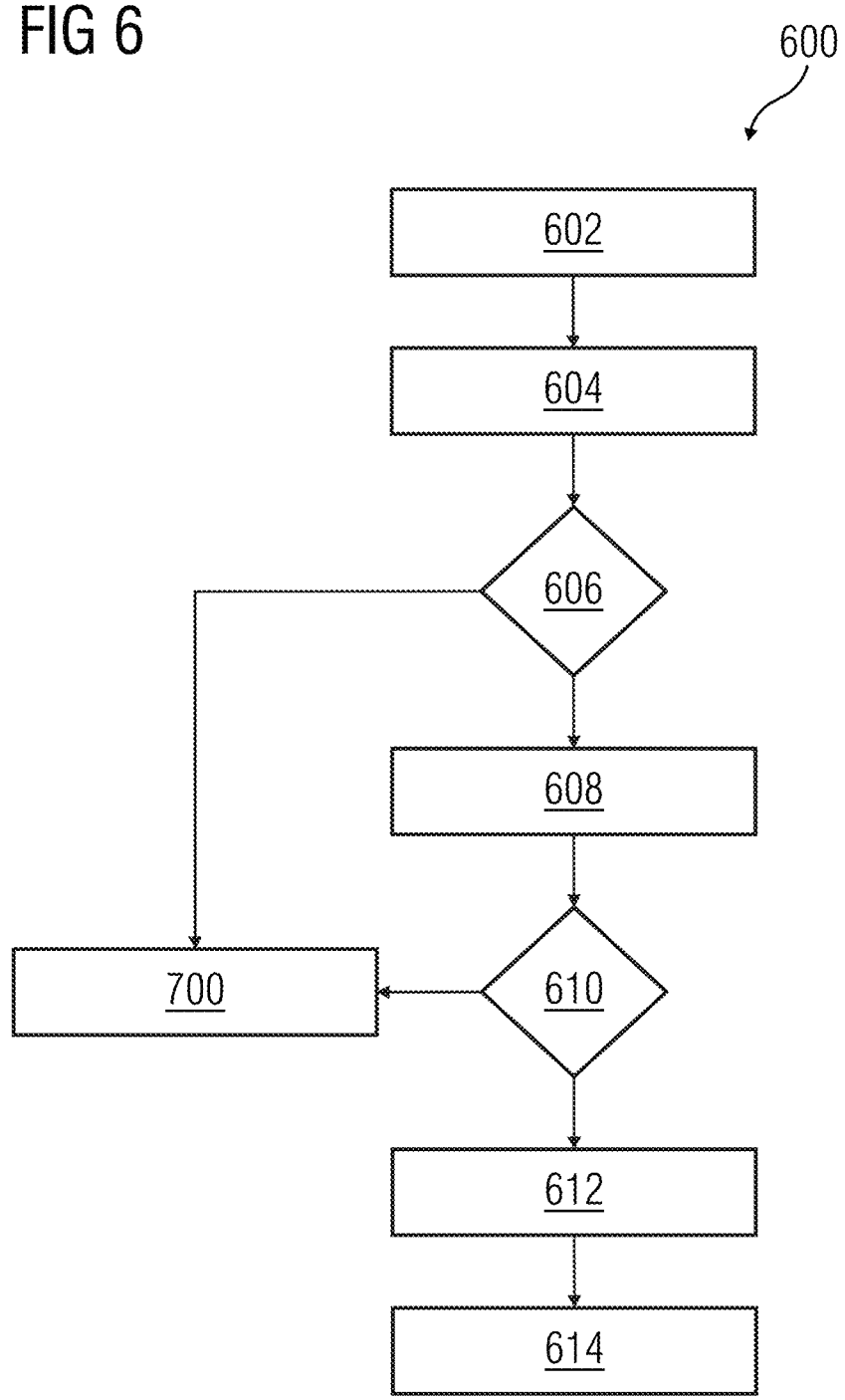
FIG. 6 illustrates a flowchart depicting acts of a method for determining a cluster from the plurality of clusters, in accordance with an embodiment.

Referring to FIG. 6, flowchart 600 depicts act of a method for determining a cluster from the plurality of clusters, in accordance with an embodiment of the present disclosure. At act 602, one or more features of the received imaging protocol are determined. The term "features," as used herein, refers to attributes of the imaging protocol that represent the clinical intent of the imaging protocol. Herein, the features include textual attributes of the imaging protocol and numerical attributes of the imaging protocol. In an example, the textual features may include LevelsName, Anatomical region, body size, window, and so forth. Furthermore, the numerical features may include CTDIvolmGy, EffmAs, QualityRefmAs, and so forth. Such features are extracted from the received imaging protocol. The one or more features may be extracted from the imaging protocol using natural language processing techniques known in the art. Table 1 represents a feature set that may be extracted from the received imaging protocol:

TABLE 1

| | Text Attributes | | Numerical Attributes |
|---|---|---|---|
| LevelsName | Describes the higher-level category of the Scan Protocols | CTDIvolmGy | Average Radiation Dose/Pitch factor |
| Anatomical Region | Body Part | EffmAs | Tube current time/Pitch factor |
| BodySize | Adult/Child | QualityRefmAs | It defines the overall image quality of the scan protocol currently being used |
| Window | It is used for adjusting the brightness and contrast of an image during reconstruction | | |

At act 604, a distance variation is calculated between the received imaging protocol and each of the harmonized imaging protocols associated with the plurality of clusters based on the determined one or more features. Notably, the distance variation is calculated between each of the textual attributes and numerical attributes of the received imaging protocols and each of the textual attributes and numerical attributes of the harmonized imaging protocols. In an embodiment, the maximum and minimum values of the numerical parameters (as depicted in Table 1) are calculated from the fetched data for normalizing the numerical parameters in [0,1]. For the sake of simplicity, let us consider two imaging protocols "i" and "j" and calculate the distance variation between $i^{th}$ and $j^{th}$ imaging protocols. In an example, $i^{th}$ imaging protocol is the received imaging protocol and the $j^{th}$ imaging protocol is one of the harmonized imaging protocols stored in the first database 108.

In an exemplary implementation, for a numerical feature "f," distance variation is the ratio of absolute difference feature f ($f_i$ & $f_j$) of $i^{th}$ & $j^{th}$ protocols and maximum range observed from all individual protocols. So, total distance variation between all numerical features f between $i^{th}$ & $j^{th}$ protocols is calculated as:

$$\text{num\_}d_{ij}=\Sigma_f |f_i-f_j|*weight_f/|\max(N_f)-\min(N_f)|$$

wherein, the summation is over all numerical features f; $N_f$ is the set of feature f of all the harmonized imaging protocols in the database; and $weight_f$ is the weight assigned to feature f in [0,1].

Furthermore, for a textual feature f, distance variation ($d_{ij}$) equals 1 only when features $f_i$ & $f_j$ have different value. In case, the features $f_i$ & $f_j$ have same value, then distance variation ($d_{ij}$) equals 0. Therefore, the distance variation between all textual features f between $i^{th}$ & $j^{th}$ protocols is calculated as:

$$\text{cat\_}d_{ij} = \frac{\sum_f (d_{ij} * weight_f)}{\sum_f weight_f}$$

wherein, the summation is over all textual features f.

Subsequently, the total distance between $i^{th}$ & $j^{th}$ imaging protocols is calculated as:

$$d=\text{num\_}d_{ij}+\text{cat\_}d_{ij}$$

At act 606, each of the calculated distance variation values are compared with a second threshold value. The second threshold value is a quantitative measure of degree of closeness of between the $i^{th}$ & $j^{th}$ imaging protocols. The second threshold value may be a value below which the association between $i^{th}$ & $j^{th}$ to imaging protocols is not possible. At act 608, a decision is made whether the calculated distance variation is above the second threshold value or below the second threshold value. When the calculated distance variation is above the second threshold value, then act 610 is executed. When the calculated distance variation is below the second threshold value, then act 700 is executed.

At act 610, one or more harmonized imaging protocols having the distance variation above the second threshold value are determined. There may be more than one harmonized imaging protocols for which the calculated distance variation is above a threshold value. However, one imaging protocol may only be associated with only one harmonized imaging protocol. Henceforth, at act 612, a decision is made whether the determined one or more harmonized imaging protocols belong to the same cluster or not. In a case, when the determined one or more harmonized imaging protocols belong to the same cluster, then act 614 is executed. In another case, when the determined one or more harmonized imaging protocols do not belong to the same cluster, then act 600 is executed.

At act 614, when the one or more harmonized imaging protocols belong to the same cluster, then the corresponding cluster is selected.

Figure 7:
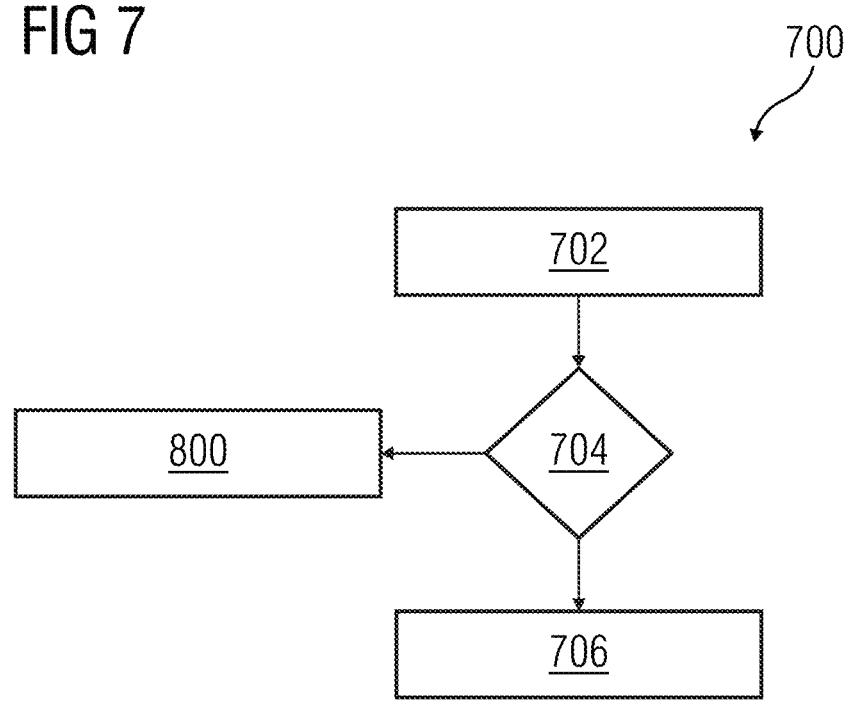
FIG. 7 illustrates a flowchart depicting acts of a method for determining a cluster from the plurality of clusters, in accordance with another embodiment.

Referring to FIG. 7, flowchart 700 depicts acts of a method for determining a cluster from the plurality of clusters, in accordance with another embodiment of the present disclosure. As stated in FIG. 6, the method 700 is executed when the calculated distance variation is below the second threshold value. Also, the method 700 is executed when the determined one or more harmonized imaging protocols do not belong to the same cluster.

At act 702, a difference between each of the numerical features of the imaging protocol and the numerical features of each of the one or more harmonized imaging protocols is calculated, when the one or more harmonized imaging protocols do not belong to the same cluster.

At act 704, the calculated difference is compared to a third threshold value. Herein, it is determined whether the calculated difference is below the third threshold value or not. In an example, the third threshold value is 1 and the comparison is determined as below:

$$|diff_{num\_features}| < 1$$

In case the calculated difference is below the third threshold value, then act 706 is executed. In another case when the calculated difference is above the third threshold value, then method acts 800 are executed.

At act 706, the at least one harmonized imaging protocol having the calculated difference below the third threshold value is determined. Further, the cluster associated with the determined at least one imaging protocol is selected.

Figure 8:
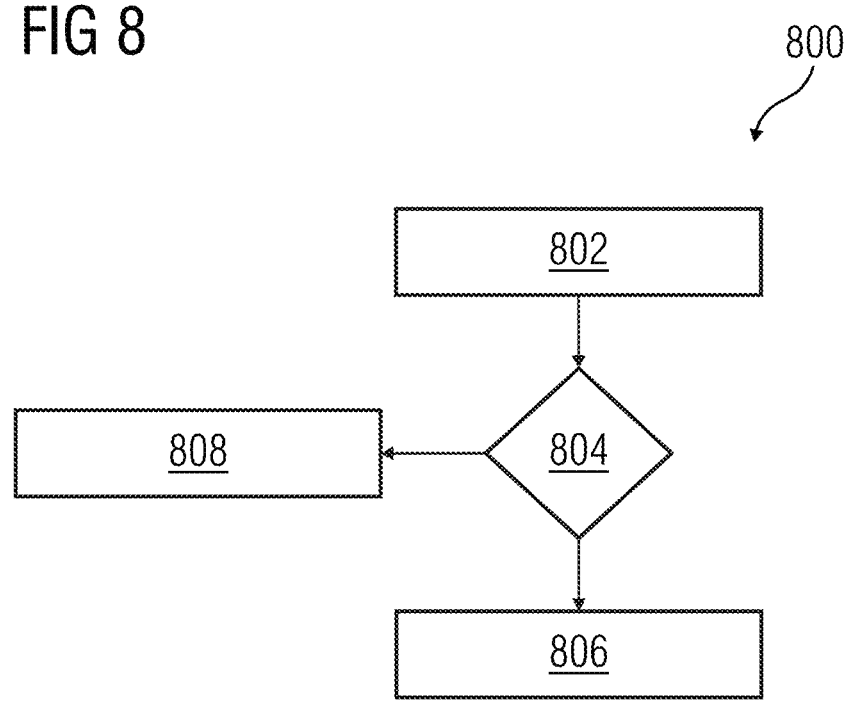
FIG. 8 illustrates a flowchart depicting acts of a method for determining a cluster from the plurality of clusters, in accordance with another embodiment.

Referring to FIG. 8, flowchart 800 depicts acts of a method for determining a cluster from the plurality of clusters, in accordance with another embodiment of the present disclosure.

At act 802, slope variation between the obtained imaging protocol and each of the one or more harmonized imaging protocols is calculated when the calculated difference is above a threshold value. In an example, difference between the numerical features of the received imaging protocol and the numerical features of the selected imaging protocols are calculated as below:

$$d_C = \text{Customized Protocol}_{CTDI} - \text{Selected Protocols}_{CTDI}$$

$$d_Q = \text{Customized Protocol}_{QualityRefmAs} - \text{Selected Protocols}_{QualityRefmAs}$$

$$d_E = \text{Customized Protocol}_{EffmAs} - \text{Selected Protocols}_{EffmAs}$$

Furthermore, using the values of above calculated difference, the slope variation is calculated as below:

$$= \begin{cases} (|d_C|+|d_Q|)*(|d_C|+|d_E|)/d_c^2 & , \text{sgn}(d_Q) = \text{sgn}(d_E) = \text{sgn}(d_C) \\ -(|d_C|+|d_Q|)*(|d_C|+|d_E|)/d_c^2 & , \text{sgn}(d_Q) = \text{sgn}(d_E) \neq \text{sgn}(d_C) \\ (|d_C|+|d_Q|+|d_E|)*s*\text{sgn}(d_C)/|d_C| & , (-1 < d_Q < 1)|(-1 < d_E < 1) \\ l & , -1 \leq d_C \leq 1 \\ (|d_C|+|d_Q|)*(|d_C|+|d_E|)*\text{sgn}(d_C*d_Q*d_E)/d_c^2 & , \text{otherwise} \end{cases}$$

wherein, $$l = \begin{cases} \max(|d_Q|, |d_E|), & (|d_Q| > |d_E|^2)|(|d_E| > |d_Q|^2) \\ \min(|d_Q|, |d_E|), & \text{otherwise} \end{cases};$$

$$s = \begin{cases} \text{sgn}(d_Q), & |d_Q| \geq |d_E| \\ \text{sgn}(d_E), & \text{otherwise} \end{cases}$$

$$\text{Slope\_Variation} = \begin{cases} nan, & b \leq -1/3 \\ b, & b > -1/3 \end{cases}$$

At act 804, it is determined whether there is any harmonized imaging protocol having a calculated slope variation below a fourth threshold value. The fourth threshold value is a value below which no harmonized imaging protocol exists in the first database 108. In a case when there is at least one standard imaging protocol having a calculated slope variation above the fourth threshold value, then act 806 is executed. In another case, when there is no harmonized imaging protocol having a calculated slope variation below a fourth threshold value, then act 808 is calculated.

At act 806, the cluster associated with the determined harmonized imaging protocol is selected. At act 808, a new cluster for the received imaging protocol is generated based on the set of imaging parameters, when the calculated slope variation is above the fourth threshold value. Advantageously, a new cluster is created in case the first database 108 does not include a harmonized imaging protocol having a clinical intent similar to that of the received imaging protocol. In other words, when there is no corresponding RPID for the received imaging protocol found in the first database 108, then a new cluster is generated. According to an embodiment, an imaging protocol identifier is also determined for the generated cluster based on a predefined set of rules. The predefined set of rules may be used for generating name tags or imaging protocol identifiers for the new cluster. The nomenclature of the imaging identifiers is based on the predefined set of rules. Herein, the predefined set of rules may include rules for deciding anatomical nomenclature which is defined in a hierarchical manner. In an example, Anatomical-Hierarchical Naming Convention is used to generate name tags for the clusters. Furthermore, the imaging identifier of the customized imaging protocol when available may be appended with patient specific information, wherein the patient specific information includes at least one of: age of the patient and weight of the patient.

In an example, using the Anatomical-Hierarchical Naming Convention, a structured database or a dictionary is created for anatomy, sub-anatomy, process, or study type levels for describing the hierarchy in the nomenclature of the imaging identifiers. The multiple levels information obtained from the imaging protocol name and categorical data is arranged using the dictionary for maintaining the hierarchy. Furthermore, additional study details and patient information are appended with the hierarchy for creating the name tags or imaging identifiers for the imaging protocols that are associated with the new cluster.

For example, consider a protocol name "CAP_W_1_25_LBS.Child" as shown in Table 2 (wherein RPID249 in the Radlex corresponds to "CT CHEST ABDOMEN PELVIS WITH IV CONTRAST").

TABLE 2

| Protocol Name | RPID Mapping | Anatomical-Hierarchical |
| --- | --- | --- |
| CAP_W_1_25_LBS.Child | RPID249_Child | CAP_W/OC_Child.1-25_LBS |

In an example, exact RPID match is when the combined string matches with a particular RPID from the Radlex Playbook, for example, the mapping score is 1 in this case (as shown in Table 3).

TABLE 3

| Protocol Name | Combined String | RPID Mapping |
| --- | --- | --- |
| AbdomenRoutine.Adult | abdomen | RPID188_Adult |

Furthermore, hierarchical mapping is used when there is no strong match (for example, the mapping score <0.3) between received imaging protocol and the database 108, as depicted in Table 4.

TABLE 4

| Protocol Name | Combined String | Hierarchical Mapping |
| --- | --- | --- |
| BodyPCTSeq.Adult | perfusion sequential | Body_Abdomen_Perfusion_Adult |

The present disclosure may take the form of a computer program product including program modules accessible from computer-usable or computer-readable medium storing program code for use by or in connection with one or more computers, processors, or instruction execution system. For the purpose of this description, a computer-usable or computer-readable medium is any apparatus that may contain, store, communicate, propagate, or transport the program for use by or in connection with the instruction execution system, apparatus, or device. The medium may be electronic, magnetic, optical, electromagnetic, infrared, or semiconductor system (or apparatus or device) or propagation mediums in and of themselves as signal carriers are not included in the definition of physical computer-readable medium include a semiconductor or solid state memory, magnetic tape, a removable computer diskette, random access memory (RAM), a read only memory (ROM), a rigid magnetic disk and optical disk such as compact disk read-only memory (CD-ROM), compact disk read/write, and DVD. Both processors and program code for implementing each aspect of the technology may be centralized or distributed (or a combination thereof) as known to those skilled in the art.

The present disclosure aims at providing a system and a method for recommending at least one imaging protocol for scanning a patient. The present disclosure provides a method for harmonizing the imaging protocols across different imaging modalities (such as CT scanners) and different healthcare institutions by determining a standardized name tags by defining a set of rules for nomenclature. Advantageously, different imaging protocols that are customized by radiologists may be harmonized to clearly represent clinical intent of the imaging protocol. Furthermore, the disclosure also aims at recommending harmonized imaging protocols to the radiologists for scanning the patient. Such a method provides that the user (radiologists, clinicians, etc.) may access the protocols with similar clinical intent across different scanners and compare the imaging protocols with the other clinical intent protocols available on other scanner/models. The present disclosure also aims to effectively and efficiently harmonize the imaging protocols and assign the standard nomenclature for the imaging protocols that have been customized by the radiologists. Beneficially, the present disclosure aids the clinical institutes in identifying the right clinical intent of the imaging protocol and avoid creating multiple protocols with same parameters for the same clinical intent. Therefore, the radiologists may choose protocol options from the provided list of imaging protocols to perform clinical scan which saves time for tuning the scanner parameters, thereby making the scanning procedure faster and effective. Furthermore, the clinical intent of the imaging protocol is also mapped to the standard convention to facilitate high level of inter-operability.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the disclosure has been illustrated and described in detail with the help of the embodiments, the disclosure is not limited to the disclosed examples. Other variations may be deduced by those skilled in the art without leaving the scope of protection of the claimed disclosure.

The invention claimed is:

1. A method for recommending at least one imaging protocol for scanning a patient, the method comprising:
receiving, by a processor, an imaging protocol, wherein the imaging protocol comprises information pertaining to a set of imaging parameters for imaging the patient;
mapping the received imaging protocol to an imaging identifier based on plurality of standard imaging protocols stored in a second database;
determining a mapping score of the mapping between the received imaging protocol and the mapped imaging identifier based on an accuracy of the mapping;
determining a cluster from a plurality of clusters stored in a first database when the mapping score is below a first threshold value, wherein each cluster in the plurality of clusters is associated with a harmonized imaging protocol based on a clinical intent of the information; and
determining at least one imaging identifier associated with the determined cluster, wherein the determined at least one imaging identifier is one imaging identifier out of a plurality of imaging identifiers stored in the first database, wherein the first database comprises a plurality of harmonized imaging protocols, wherein each harmonized imaging protocol of the plurality of harmonized imaging protocols is associated with at least one imaging identifier out of the plurality of imaging identifiers, and wherein the plurality of imaging identifiers represents a clinical intent of the associated imaging protocol;

determining at least one harmonized imaging protocol out of the plurality of harmonized imaging protocols based on the determined at least one imaging identifier; and providing the determined at least one harmonized imaging protocol on a graphical user interface.

2. The method of claim 1, wherein providing the determined at least one harmonized imaging protocol comprises recommending the determined at least one harmonized imaging protocol for scanning the patient, and wherein the determined at least one harmonized imaging protocol is presented in a hierarchical manner.

3. The method of claim 1, further comprising:

obtaining, by the processor, a plurality of standard imaging protocols from one or more sources;

clustering each standard imaging protocol of the plurality of standard imaging protocols into a cluster based on a clinical intent of the standard imaging protocols;

harmonizing each standard imaging protocol of the plurality of standard imaging protocols in each cluster with an imaging identifier and patient specific information; and storing the harmonized standard imaging protocols in the first database in a hierarchical manner based on a predefined set of rules.

4. The method of claim 1, wherein the determining of the cluster from the plurality of clusters comprises determining one or more features of the received imaging protocol, wherein the one or more features comprise textual attributes of the imaging protocol and numerical attributes of the imaging protocol.

5. The method of claim 4, wherein the determining of the cluster from the plurality of clusters further comprises:

calculating a distance variation between the received imaging protocol and each harmonized imaging protocol of the harmonized imaging protocols associated with the plurality of clusters based on the determined one or more features;

comparing each calculated distance variation with a second threshold value;

determining one or more harmonized imaging protocols having the distance variation above the second threshold value;

determining whether the one or more harmonized imaging protocols belong to a same cluster; and selecting the cluster when the one or more harmonized imaging protocols belong to the same cluster.

6. The method of claim 5, wherein the determining of the cluster from the plurality of clusters further comprises:

calculating a difference between each numerical feature of the imaging protocol and the numerical features of each harmonized imaging protocol of the one or more harmonized imaging protocols when the one or more harmonized imaging protocols do not belong to the same cluster;

determining at least one harmonized imaging protocol having the calculated difference below a third threshold value; and selecting the cluster associated with the determined at least one harmonized imaging protocol.

7. The method of claim 6, wherein the determining of the cluster from the plurality of clusters further comprises:

calculating a slope variation between the received imaging protocol and each harmonized imaging protocol of the one or more harmonized imaging protocols when the calculated difference is above a fourth threshold value;

determining a harmonized imaging protocol having a calculated slope variation below the fourth threshold value; and selecting the cluster associated with the determined harmonized imaging protocol.

8. The method of claim 7, further comprising:

generating a cluster for the received imaging protocol based on the set of imaging parameters when the calculated slope variation is above the fourth threshold value.

9. The method of claim 8, further comprising:

determining an imaging identifier for the generated cluster based on a predefined set of rules.

10. The method of claim 1, further comprising:

determining an imaging identifier for the imaging protocol based on the second database when the mapping score is above the first threshold value.

11. The method of claim 9, further comprising:

appending the imaging identifier associated with the imaging protocol with patient specific information, wherein the patient specific information comprises an age of the patient, a weight of the patient, or a combination thereof.

12. An apparatus for recommending at least one imaging protocol for scanning a patient, the apparatus comprising:

at least one processor; and a memory communicatively coupled to the at least one processor, wherein the memory is configured to:

receive an imaging protocol comprising information pertaining to a set of imaging parameters for imaging the patient;

map the received imaging protocol to an imaging identifier based on plurality of standard imaging protocols stored in a second database;

determine a mapping score of the mapping between the received imaging protocol and the mapped imaging identifier based on an accuracy of the mapping;

determine a cluster from a plurality of clusters stored in a first database when the mapping score is below a first threshold value, wherein each cluster in the plurality of clusters is associated with a harmonized imaging protocol based on a clinical intent of the information;

determine at least one imaging identifier associated with the determined cluster, wherein the determined at least one imaging identifier is one imaging identifier out of a plurality of imaging identifiers stored in the first database, wherein the first database comprises a plurality of harmonized imaging protocols, wherein each harmonized imaging protocol of the plurality of harmonized imaging protocols is associated with at least one imaging identifier out of the plurality of imaging identifiers, and wherein the plurality of imaging identifiers represent a clinical intent of the associated imaging protocol;

determine at least one harmonized imaging protocol out of the plurality of harmonized imaging protocols based on the determined at least one imaging identifier; and provide the determined at least one harmonized imaging protocol on a graphical user interface.

13. The apparatus of claim 12, wherein, in the providing of the determined at least one harmonized imaging protocol, the memory is configured to recommend the determined at least one harmonized imaging protocol for scanning the patient, and wherein the determined at least one harmonized protocol is presented in a hierarchical manner.

14. The apparatus of claim 12, wherein the memory is further configured to:

obtain a plurality of standard imaging protocols from one or more sources;

cluster each standard imaging protocol of the plurality of standard imaging protocols into a cluster based on a clinical intent of the plurality of standard imaging protocols;

harmonize each standard imaging protocol of the plurality of standard imaging protocols in each cluster with an imaging identifier and patient specific information; and store the harmonized imaging protocols in the first database in a hierarchical manner based on a predefined set of rules.

15. The apparatus of claim 12, wherein, in the determining of the cluster from a plurality of clusters, the memory is configured to determine one or more features of the received imaging protocol, wherein the one or more features comprise textual attributes of the imaging protocol and numerical attributes of the imaging protocol.

16. The apparatus of claim 15, wherein, in the determining of the cluster from the plurality of clusters, the memory is further configured to:

calculate a distance variation between the received imaging protocol and each harmonized imaging protocol of the harmonized imaging protocols associated with the plurality of clusters based on the determined one or more features;

compare each calculated distance variation with a second threshold value;

determine one or more harmonized imaging protocols having the distance variation above the second threshold value;

determine whether the one or more harmonized imaging protocols belong to a same cluster; and select the cluster when the one or more harmonized imaging protocols belong to the same cluster.

17. The apparatus of claim 16, wherein, in the determining of the cluster from the plurality of clusters, the memory is further configured to:

calculate a difference between each numerical feature of the numerical features of the imaging protocol and the numerical features of each harmonized imaging protocol of the one or more harmonized imaging protocols when the one or more harmonized imaging protocols do not belong to the same cluster;

determine at least one harmonized imaging protocol having the calculated difference below a third threshold value; and select the cluster associated with the determined at least one harmonized imaging protocol.

18. The apparatus of claim 17, wherein, in the determining of the cluster from the plurality of clusters, the memory is further configured to:

calculate a slope variation between the received imaging protocol and each harmonized imaging protocol of the one or more harmonized imaging protocols when the calculated difference is above a fourth threshold value;

determine a harmonized imaging protocol having a calculated slope variation below the fourth threshold value; and select the cluster associated with the determined harmonized imaging protocol.

19. A system for recommending at least one imaging protocol for scanning a patient, the system comprising:

a first database comprising a plurality of harmonized imaging protocols;

a second database comprising a plurality of standard imaging protocols; and an apparatus for recommending the at least one imaging protocol for scanning the patient, the apparatus comprising:

at least one processor; and a memory communicatively coupled to the at least one processor, wherein the memory is configured to:

receive an imaging protocol comprising information pertaining to set of imaging parameters for imaging the patient;

map the received imaging protocol to an imaging identifier based on plurality of standard imaging protocols stored in the second database;

determine a mapping score of the mapping between the received imaging protocol and the mapped imaging identifier based on an accuracy of the mapping;

determine a cluster from a plurality of clusters stored in the first database when the mapping score is below a first threshold value, wherein each cluster in the plurality of clusters is associated with a harmonized imaging protocol based on a clinical intent of the information;

determine at least one imaging identifier associated with the determined cluster, wherein the determined at least one imaging identifier is one imaging identifier out of a plurality of imaging identifiers stored in the first database, wherein the first database comprises a plurality of harmonized imaging protocols, wherein each harmonized imaging protocol of the plurality of harmonized imaging protocols is associated with at least one imaging identifier out of the plurality of imaging identifiers, and wherein the plurality of imaging identifiers represent a clinical intent of the associated imaging protocol;

determine at least one harmonized imaging protocol out of the plurality of harmonized imaging protocols based on the determined at least one imaging identifier; and provide the determined at least one harmonized imaging protocol on a graphical user interface.

\* \* \* \* \*